(12) United States Patent
Lovoi

(10) Patent No.: US 6,987,835 B2
(45) Date of Patent: Jan. 17, 2006

(54) MINIATURE X-RAY TUBE WITH MICRO CATHODE

(75) Inventor: Paul A. Lovoi, Saratoga, CA (US)

(73) Assignee: Xoft MicroTube, Inc., Fremont, CA (US)

(*) Notice: Subject to any disclaimer, the term of this patent is extended or adjusted under 35 U.S.C. 154(b) by 204 days.

(21) Appl. No.: 10/397,498

(22) Filed: Mar. 26, 2003

(65) Prior Publication Data

US 2004/0192997 A1 Sep. 30, 2004

(51) Int. Cl.
*H01J 35/06* (2006.01)
*H01J 35/32* (2006.01)
*H01J 9/04* (2006.01)
*A61N 5/10* (2006.01)

(52) U.S. Cl. .................. 378/136; 378/64; 378/65; 378/119; 378/121; 445/28

(58) Field of Classification Search .......... 378/64, 378/65, 91, 119, 121, 136, 137, 138; 445/28
See application file for complete search history.

(56) References Cited

U.S. PATENT DOCUMENTS 5,090,043 A * 2/1992 Parker et al. ............... 378/121
5,773,921 A * 6/1998 Keesmann et al. ......... 313/309
6,134,300 A * 10/2000 Trebes et al. ............... 378/136
6,438,207 B1 * 8/2002 Chidester et al. ........... 378/138
6,661,875 B2 * 12/2003 Greenwald et al. ......... 378/119

* cited by examiner

*Primary Examiner*—Allen C. Ho
(74) *Attorney, Agent, or Firm*—Thomas M. Freiburger

(57) ABSTRACT

A miniature x-ray tube capable of intra vascular use, has a micro cathode preferably formed by MEMS techniques. The very fine wire of the cathode filament is formed on a semiconductor base and draws a current sufficiently low that lead wires in a cathode heater circuit, passing through a probe line connected to the x-ray tube, can be very small wires, which helps maintain sufficient dielectric spacing in the high voltage circuit handled by the same probe line. In a preferred embodiment the probe line comprises a glass fiber, held at a small diameter to allow flexibility for navigating small-radius turns within the vessels. In a preferred embodiment the fiber is overcoated with a high-dielectric polymer to significantly increase the dielectric strength of the overall cable, without adding significantly to stiffness. The high voltage ground conductor is a coaxial sheath on the outside of the polymer. Exterior to the ground conductor is a further flexible layer having paths for coolant.

32 Claims, 6 Drawing Sheets

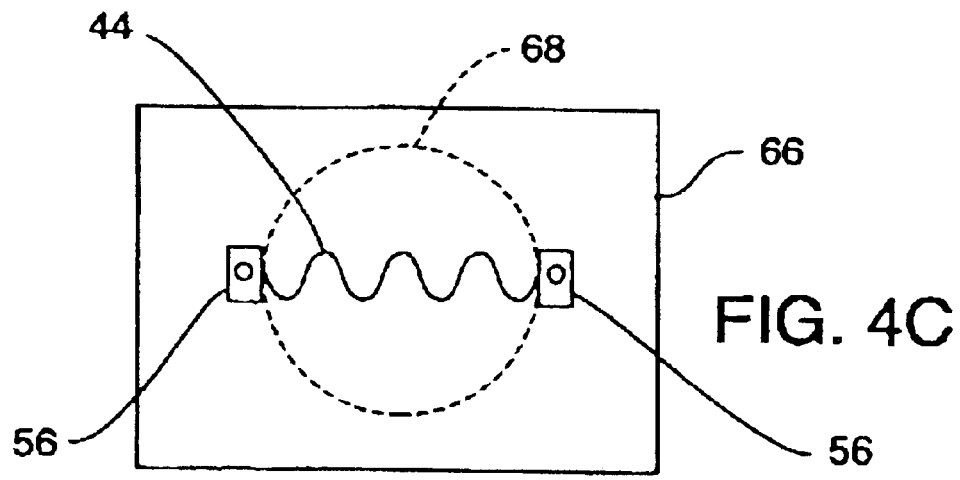
FIG. 4C
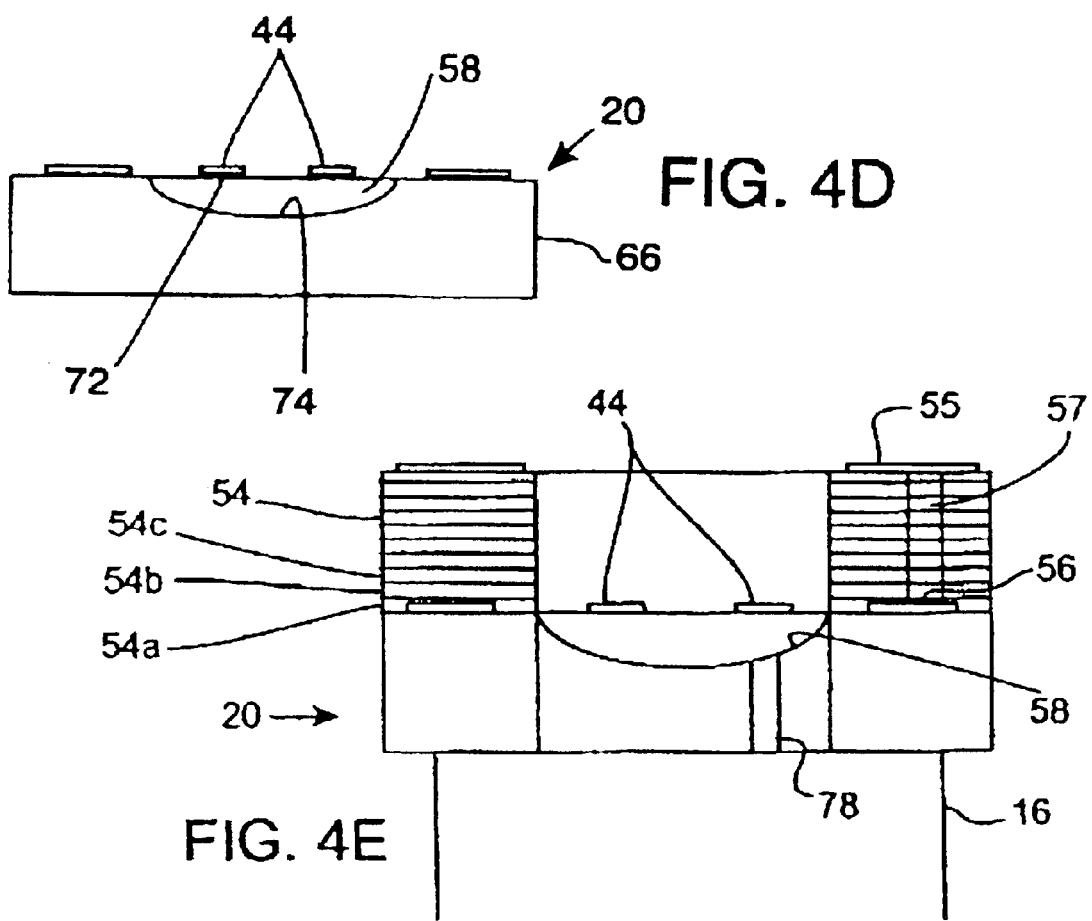
FIG. 4D
FIG. 4E

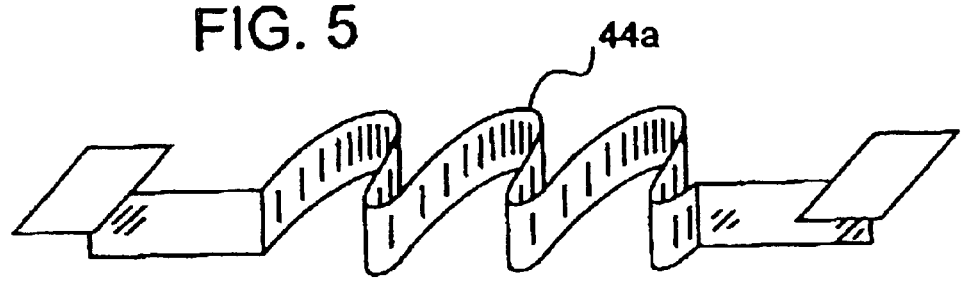
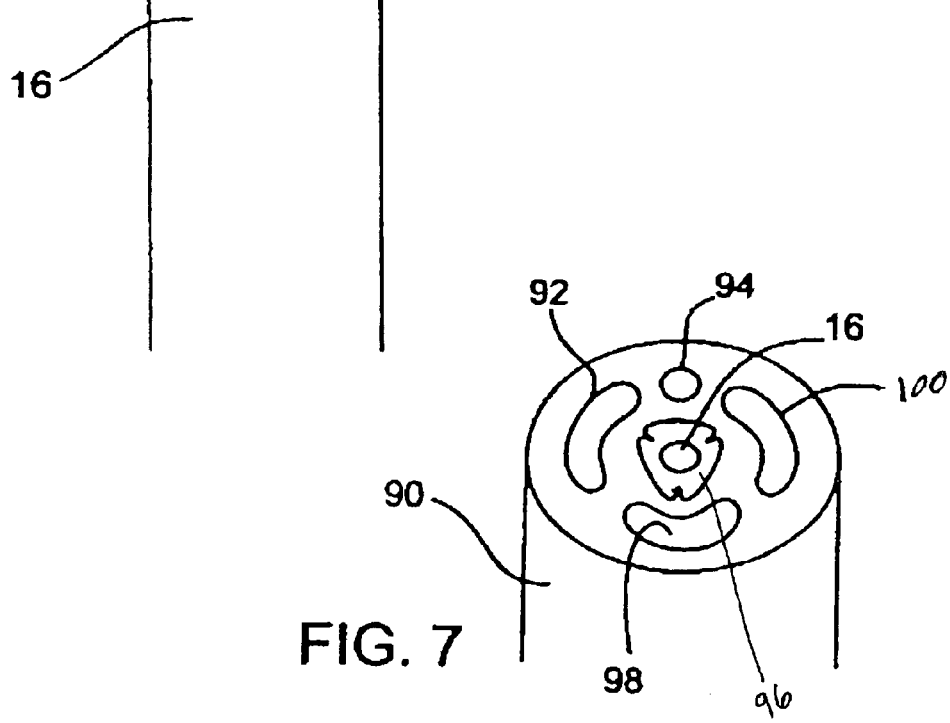

MINIATURE X-RAY TUBE WITH MICRO CATHODE

BACKGROUND OF THE INVENTION

The invention is concerned with a miniature x-ray tube on a probe, for use in narrow lumens such as human blood vessels, or with an applicator in natural or surgical cavities, for delivering an x-ray dosage. More specifically the invention is directed at such an x-ray tube including a micro cathode formed by MEMS techniques.

A miniature x-ray tube is disclosed in Xoft Microtube U.S. Pat. No. 6,319,188, and that disclosure is incorporated herein by reference. As explained in that patent, it is sometimes desirable to irradiate the interior walls of blood vessels following balloon angioplasty or the implantation of a stent. Such radiation, which has in the past been administered by radioactive isotopes at the end of probes, has been found useful in prevention and treatment of restenosis. Other cavities or passages, both surgical and natural, can also be beneficially treated by x-ray, provided the source is relatively small.

Much of the previous effort for miniature x-ray tubes has focused on field emission cathodes. Field emission cathodes (gated and non-gated) have a number of disadvantages including extreme vacuum requirements; very short lifetimes in high voltage x-ray tubes due to ion milling of the cathode; lack of robustness from tube arcs, which are common in high voltage x-ray tubes; anode to cathode spacing requirements; and limited x-ray tube output. The high vacuum requirement is especially severe in gated types since the surface to volume ratio for these small sources is so large and space for getter material is limited. Thermionic cathodes, on the other hand, are tolerant of poor vacuum conditions and tube arcs.

In fabricating a functional, reliable and efficient miniature thermionic cathode x-ray tube for such purposes, the size of the x-ray tube at the end of the probe, and the functional considerations for the device both in operation and for insertion, dictate a number of limitations. The tube itself must be very small in diameter: for lumens, on the order of about 1.00 to 1.25 millimeter in external diameter, and less than 9 mm in length, preferably 5–6 mm; for other cavities, generally about 2–3 mm in diameter. The probe cable for lumens is required to be very flexible, capable of turning around a radius on the order of about one centimeter, which generally dictates that the probe diameter and length be small. High voltage must be carried in the probe cable over two conductors connected to a cathode and an anode of the x-ray tube, with sufficient insulation and spacing to prevent dielectric breakdown. The thermionic cathode is required to operate on very small current, or else the conductors within the probe cable serving the cathode heating circuit will need a large cross section, and this can compromise the spacing between the high voltage conductors and ground, thus compromising dielectric integrity or necessitating a larger diameter in the probe. A diameter larger than about 1 mm to 1.25 mm, or reduced cable flexibility, will compromise the usefulness of the x-ray probe for treatment of restenosis or other small lumens or vessel indications.

All of these concerns make difficult the design and production of an effective and efficient miniature x-ray probe device using an extruded metal wire filament as a thermionic cathode. This and other issues are addressed by the invention described below.

SUMMARY OF THE INVENTION

Pursuant to the current invention, a device for use in the prevention and treatment of restenosis and for administering x-ray treatment in other body cavities or passages, comprises a miniature x-ray tube and high voltage probe cable forming an integrated system.

In one preferred embodiment the cable or probe comprises a two-conductor glass fiber providing the required high voltage insulation from the centrally-located conductors to the outside of the glass fiber. The glass fiber is covered with a surrounding plastic overcoating and a ground conductor, as a third conductor coaxial with the inner two conductors. The x-ray tube envelope in one preferred embodiment comprises a sapphire tube hermetically sealed to the glass fiber on the cathode end of the tube and to an anode assembly at the opposite end of the tube. The glass fiber completely contains the high voltage from a controller to the cathode, without joints or transitions, and it has the advantage of very high dielectric strength. In addition, the integrated cable tube approach eliminates any rigid region adjacent to the x-ray tube caused from stiff insulation which would be necessary to insulate the joint between the x-ray tube and the high voltage cable. Such an extended rigid region would make deliverability of the tube to the site difficult or impossible. The use of a glass fiber as the high voltage insulation material allows the hermetic integration of the cable with the tube and permits other uses of the optical characteristics of the fiber to provide additional benefits such as: infrared pyrometry, if desired, of the cathode temperature; dosimetry using a plastic scintillator; or surface temperature or phosphor based thermometry.

In accordance with an important feature of the invention, the x-ray tube cathode comprises a micro cathode created using MEMS technology (micro electro mechanical systems). This helps meet stringent requirements of a preferred embodiment in which the cathode has to fit within a very small working inside tube diameter, which may be about 0.7 millimeter or less, and must consume preferably less than about 0.05 watt of power, thus dictating a very small filament. The cathode preferably comprises a thin tungsten, the ribbon could alternatively be platinum or a platinum-coated material in a folded or convoluted pattern. The cathode is produced by depositing a layer of cathode filament material on an etchable semiconductor substrate, then etching away all of the metal material other than the desired filament. Further, an area of the substrate supporting the filament is etched away, such as in a dish pattern below the filament, so that the filament cathode hangs in free space with its ends supported at remaining blocks of metal material on the substrate surface.

By these MEMS techniques, extremely fine micro cathodes can be produced, having emissive output and filament lifetimes consistent with conventional electron tube technology. The low heater operating current of such a fine filament reduces the conductor size requirement in the glass fiber, and in a disclosed preferred embodiment this conductor size can be less than about 0.003 inch in diameter.

To operate the x-ray tube with the micro cathode, two cathode heating current leads need to be provided to supply the filament of the micro cathode, and for a grounded anode configuration these leads need to electrically float at the tube high voltage, requiring that both the leads be insulated from the tube ground return. These first and second electrical conductors in the heating circuit can be configured coaxially, with a center conductor and a coaxial conductor surrounded by additional glass to provide the insulation. Alternatively, a twin axial configuration can be used, providing two buried leads but with higher field gradients. A central channel with two D-shaped conductors back to back provides maximum dielectric strength with reasonable field gradients from the conductors. Other configuration are also possible, including an insulated center conductor and coating on the inside surface of the fiber for the second conductor.

An important feature in one principal embodiment of the invention is the glass fiber connecting the controller to the x-ray tube. This glass fiber provides a continuous glass path from the controller to the cathode within the x-ray tube, and involves a hermetic vacuum seal between the distal end of the glass fiber and the cathode assembly, the hermetic vacuum seal being vital in achieving short length x-ray tubes that are deliverable within the coronary arteries or other cavities or passages. In addition to providing the hermetic vacuum seal capability, the glass fiber provides needed dielectric strength as noted above for holding off the high voltage within the conductors to ground. If the fiber is made with enough glass thickness to hold off the full x-ray tube operating voltage, the fiber tends to become so thick as not to allow the short-radius bends necessary to deliver the tube to the coronary arteries or other vessels or narrow passages requiring small-radius turns. A two-layer cable is thus preferred, in which the conductors are buried within the glass fiber (or fibers) to achieve the hermetic vacuum seal to the tube, and at a small diameter that ensures flexibility. This glass fiber and a portion of the integrated x-ray tube are overcoated with a polymer, such as FEP, to provide a significant increase in the dielectric strength of the overall cable while adding little to the total cable stiffness. The diameter of each component is optimized to maximize the dielectric strength of the assembly while minimizing diameter and stiffness.

Another important feature in one embodiment of the invention is the use of a heat reflector to increase micro cathode efficiency in the miniature x-ray tube, this heat reflector also being produced by MEMS techniques. Optimizing the operation of a micro cathode for use in a miniature x-ray tube is important, because the total power dissipated by the cathode must be removed by the probe cooling system. Micro cathodes by their nature are very small devices and hence the cold portions of the structure are very close to the hot filament. In an important embodiment of the invention, a technique is used, in forming the thin micro cathode as described above, by which a heat reflector is provided behind the cathode. In depositing the metal film (e.g. tungsten) for the cathode onto the substrate, a layer of gold is first deposited, then the filament material. After the metal is etched away to form the serpentine cathode as described above, and after an area of the substrate beneath the cathode is etched away, leaving the cathode suspended in free space, the cathode is heated in a vacuum to a high enough temperature to vaporize the gold from the back of the cathode, which coats the preferably dish-shaped surface behind the cathode with a reflective coating. Such a reflector will provide high efficiency for the filament and reduce the temperature of the surrounding structure, therefore reducing outgasing when the support structure is heated.

It is thus among the objects of the invention to produce an efficient and reliable miniature x-ray tube with a micro cathode which is itself manufactured by MEMS techniques, and to produce an integrated x-ray tube and probe cable by efficient techniques in very small size, with flexibility adequate for insertion of the probe into coronary arteries or other positions requiring bends around relatively small radii. These and other objects, advantages and features of the invention will be apparent from the following description of preferred embodiments, considered along with the accompanying drawings.

DESCRIPTION OF THE DRAWINGS

FIG. 3A is a schematic end view of the probe cable, indicating a conductor coupling.

FIG. 3B is a sectional view similar to FIG. 3, showing an alternative arrangement.

FIG. 3C is another sectional view similar to FIG. 3, with a further alternative.

FIG. 3D is a similar sectional view showing another alternative.

FIGS. 4A through 4E are schematic views showing a preferred technique for production of a fine-wire cathode for the x-ray tube of the invention.

FIG. 5 is a schematic view in perspective showing another configuration for a cathode filament.

FIG. 6 is a view showing an alternative cathode/glass fiber connection arrangement including an interposer.

FIG. 7 is a schematic cross sectional view showing a complete flexible catheter assembly, with the dielectric fiber and conductors at its core.

DESCRIPTION OF PREFERRED EMBODIMENTS

Figure 1:
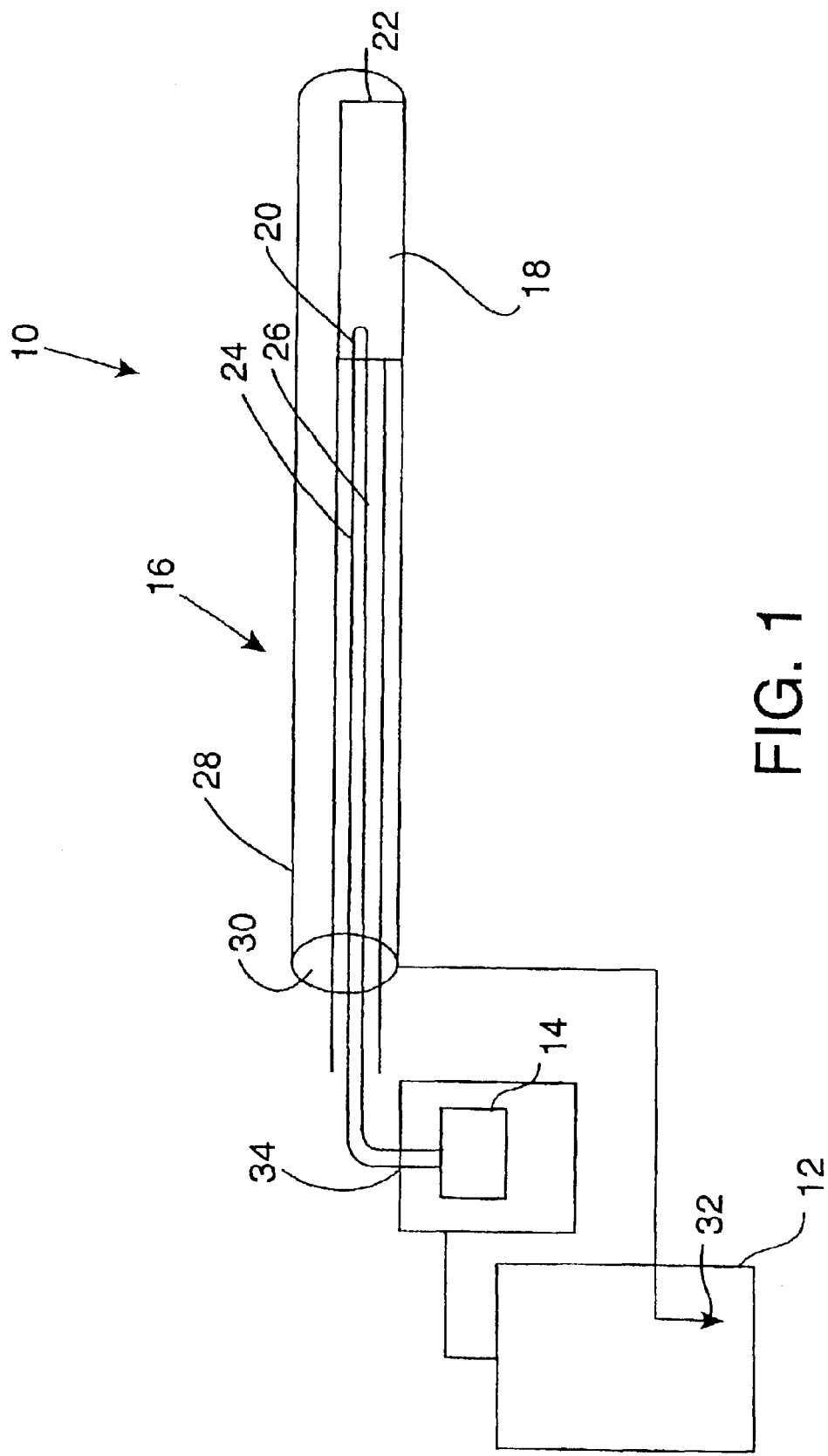
FIG. 1 is a schematic diagram indicating a system of the invention and particularly, cathode heater and x-ray tube circuits.

In the drawings, FIG. 1 shows schematically and not to scale the major elements of an x-ray device 10 for intravascular and other use in body cavities, comprising a controller 12 with high voltage power supply, a battery or other low voltage power supply 14, which can be included within the controller 12, a flexible probe line 16 extending from the controller, and a miniature x-ray tube 18 at a distal end of the flexible probe.

As indicated in this schematic drawing, the miniature x-ray tube includes a thermionic cathode 20 at a proximal end of the tube and an anode 22 at its distal end. The thermionic cathode is heated in a heater circuit involving two conductor wires 24 and 26 internal to the flexible probe line. These conductors are at low voltage relative to each other (e.g. about 2 to 50 volts), and are shown as being connected to the battery 14, although the battery could be replaced by another source of low voltage such as a transformer. These cathode heating current leads 24, 26 supply the current to heat the micro cathode 20, and these leads electrically float at the x-ray tube high voltage, which might be, for example, about negative 10 to 60 kV. This enables use of a total of three conductors in the probe line, the third conductor comprising a metallic sheath 28 arranged coaxially around and spaced outwardly from the heating current leads 24 and 26. Dielectric material lies between these leads 24, 26 and the outer, ground conductor 28, and this material is advantageously a glass fiber, indicated at 30 in the drawing. A ground is shown at 32, connected to the controller producing the high voltage.

As shown in the schematic drawing, high voltage is connected to one of the two cathode heater leads 24, 26, and the drawing shows this connection being made to the lead 24, preferably via a resister 34 providing needed isolation.

Figure 2:
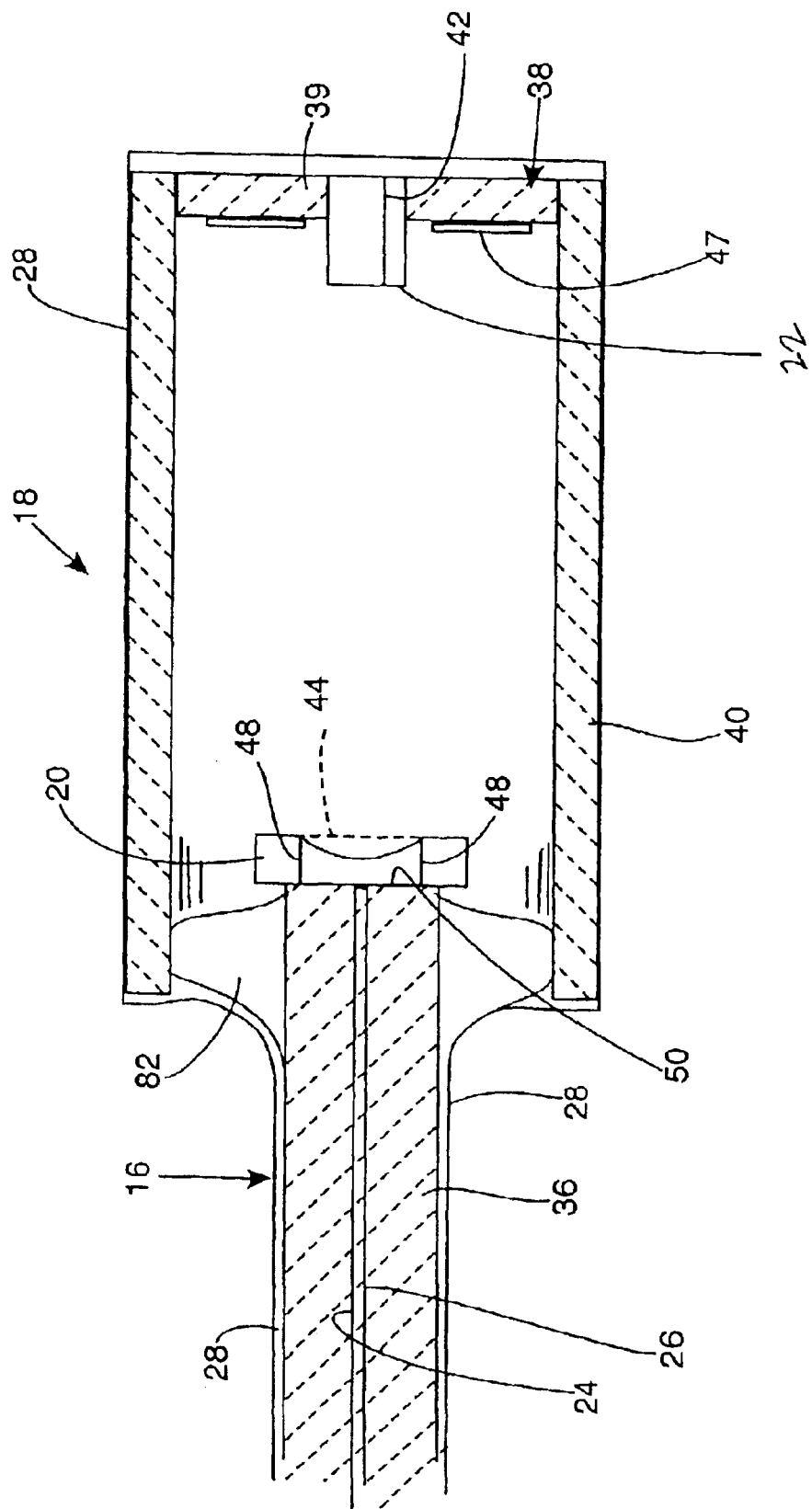
FIG. 2 is a somewhat schematic sectional view showing the x-ray tube of the invention, at the end of a flexible probe line.

FIG. 2 is a schematic representation showing the miniature x-ray tube 18, along with the distal end of the probe line 16. The entire probe line 16 is not shown, as additional layers preferably are included in a working embodiment, further described below.

The cathode heating current leads 24 and 26 are shown essentially in a central location of the probe line 16. As noted above, the probe is preferably principally comprised of a glass fiber 36. A ground coating 28 on the probe 16 and extending over the tube 18 provides the anode-side conductor, as explained above. The anode 22 is shown inside the distal end of the tube, as part of an anode assembly 38 secured to a cylindrical tube element 40, which may be formed from a sapphire. Conductive metal-filled through holes are shown at 42, for connecting the ground 28 to the anode 22. The anode assembly 38 may be based in a metal or insulator disk 39 sealed to the cylindrical x-ray tube shell 40, or the anode assembly may be as described in copending U.S. application Ser. No. 10/371,401.

A getter film 47 may be placed on the surface of the anode base 39 surrounding the anode as shown. As is well known, the getter film may be deposited by sputtering or electrophoresis.

The micro cathode assembly is indicated at 20, at the proximal end of the x-ray tube. This cathode assembly is secured by appropriate connecting means (such as glass frit bonding, brazing, laser welding, or laser braze) to the end of the glass fiber probe 16, and there can be included an interposer between these two surfaces if needed for electrical connection. In this case, FIG. 2 schematically indicates conductive metal-filled through channels 48 connecting the two heater wires 24, 26 to opposed ends of the micro cathode filament 44. Small conductive metal pads 50 may be formed on the flat distal end of the glass fiber 36, to provide ample area for effective connection of the conductors 24, 26 to the conductive channels or vias 48.

Figure 3:
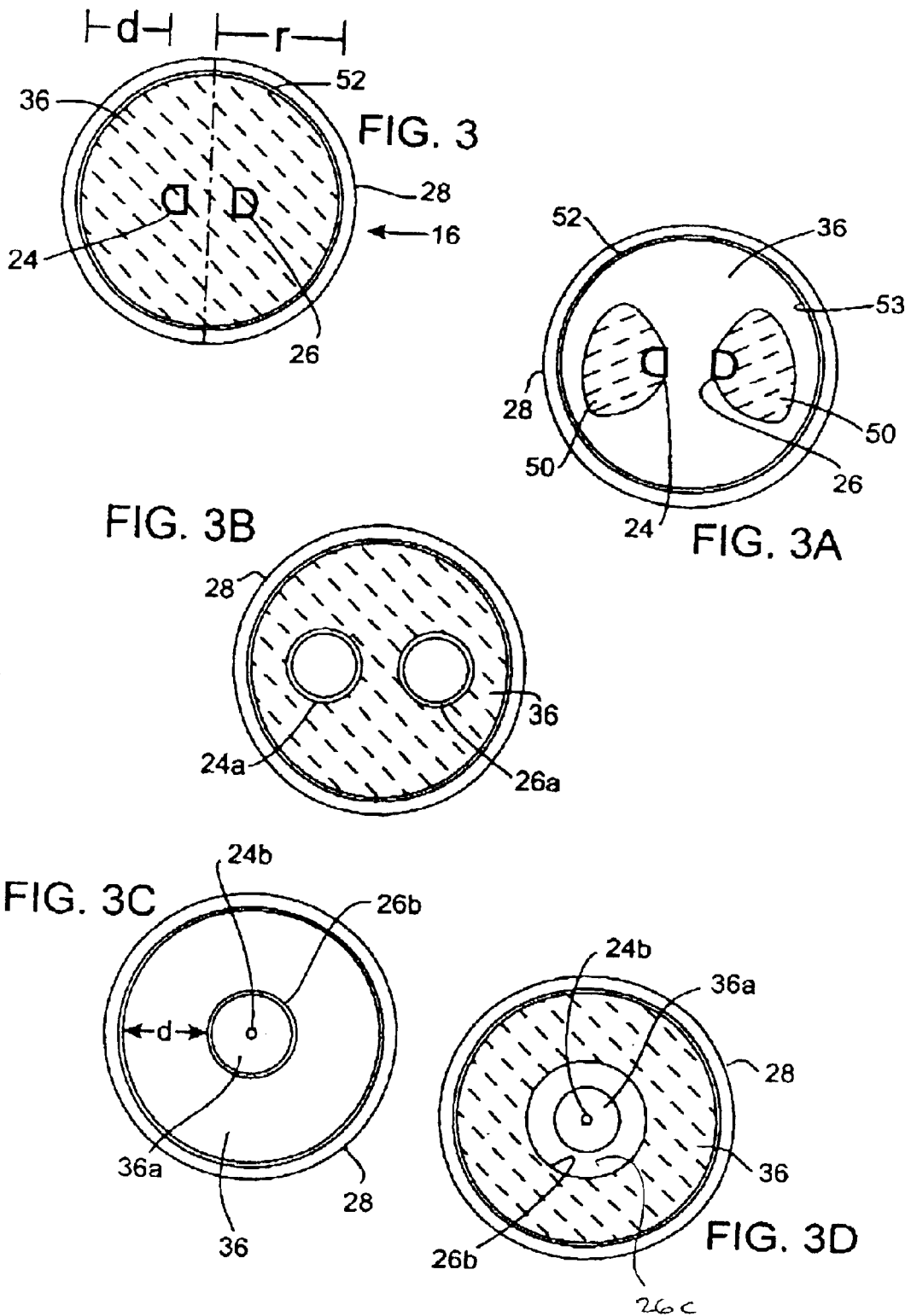
FIG. 3 is a schematic cross sectional view showing components of the flexible probe cable.

FIG. 3 shows the glass fiber probe in cross sectional view, for one preferred embodiment. As seen in that view, the heater circuit conductors 24 and 26 can comprise back-to-back D-shaped conductors, compact so as to conserve the depth of dielectric material 36, preferably glass as noted above. The distance r from the center of the probe, i.e. optical fiber, out to the periphery of the optical fiber in a preferred form is about 0.007 inch (0.18 mm). If the conductors 24 and 26 together form a diameter of about 0.004 inch, this leaves 0.005 inch for the depth d of dielectric material from each of the conductors 24 and 26 out to the ground conductor 28 circumscribing the optical fiber. If the high voltage to the x-ray tube is about 30 kV, this distance may not be quite sufficient to prevent dielectric breakdown, but in a preferred embodiment the fiber 36 is coated with a high-dielectric polymer 52 such as FEP, Teflon, or PET, which can be applied by heat shrinking to the fiber, with an adhesive layer between. During heat shrinking the adhesive melts and helps purge all air out, which is necessary to prevent arcing and breakdown. 2 to 3 mils of the polymer can add 20 kV or more dielectric strength to the composite probe, to enable a dielectric strength of 30 to 50 kV or more. The ground sheath 28 is then applied over the polymer coating.

FIG. 3A shows the distal end 53 of the probe line 36, and indicates one way for connecting the heater circuit conductors 24 and 26 to the cathode filament. This is the same technique mentioned with reference to FIG. 2, conductive metal pads 50 in contact with the ends of the conductors 24 and 26, applied by metallizing these areas at the end of the glass fiber. For example, the entire glass fiber end 53 could be metalized, then the areas outside the desired pads 50 can be etched away; or a resist could first be applied, so that when the metal is deposited, it will be only in the desired areas 50. As explained above, these pads 50 are placed in contact with the conductive vias or through holes 48 in the cathode assembly, which connect to the two ends of the cathode filament 44.

FIG. 3B shows an alternative arrangement for the cathode heater circuit conductors, here identified as 24a and 26a. In this case the conductors are simply round cross section conductors positioned side by side within the glass fiber or other dielectric material 36. This is a less efficient arrangement for these heater circuit conductors, because the minimum distance from either conductor out to the grounding sheath 28 becomes less, provided the optical fiber is maintained at a given diameter. Thus, there is greater opportunity for dielectric breakdown unless diameter of the fiber is increased, which has other disadvantages as noted above.

FIG. 3C shows another alternative arrangement wherein a pair of cathode heater circuit conductors 24b and 26b are coaxial at the center of the glass fiber 36. This configuration has certain advantages, such as ability to hermetically seal and ease of manufacture, and can result in a depth of dielectric material d which is adequate.

The coaxial approach has two features that are very attractive:

The outside of the coaxial geometry is axially symmetric like the "D" conductor, but also provides the ability to be made hermetically. A single wire 24b is hermetically coated with glass 36a and then is over coated with the second conductor 26b. This assembly is then put into the end of the fiber and sealed with a glass frit.

In a second coaxial approach shown in FIG. 3D the center conductor 24b is over coated with glass (or other insulator) 36a and the outer conductor 26b is attached to the inner wall of the fiber hole. The gap space 26c can be filled with dielectric to eliminate the air gap between high voltage and ground, or left unfilled, depending on dielectric breakdown requirements.

Figure 4:
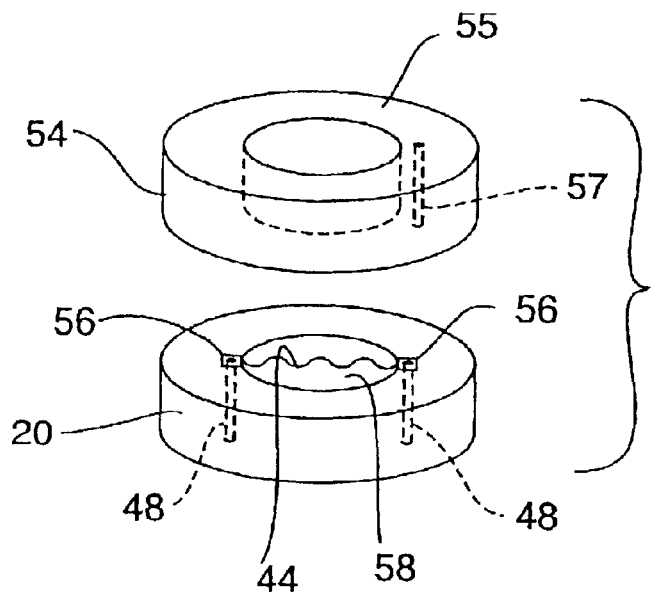
FIG. 4 is a cross sectional view showing schematically a cathode assembly which forms one end of the x-ray tube.

FIG. 4 shows the cathode assembly 20, in a preferred embodiment. Preferably the cathode assembly comprises a semiconductor disk as shown, with a diameter of about 0.3 to 0.5 mm, and with a cathode filament 44 formed as a very fine, convoluted conductor. As explained above, the cathode assembly is formed in this preferred embodiment by MEMS based technology in order to obtain a very fine cathode filament with high resistance so as to minimize required current in the cathode heater circuit. As seen in the schematic perspective of FIG. 4, an extractor cup 54 preferably is included, secured to the cathode assembly 20 and, in one embodiment, grown onto the cathode assembly as explained below. The extractor cup has a metalized ring 55 on its surface distal from the cathode, at high voltage cathode potential by a conductive via connection at 57, contacting one of two cathode base areas or support pads 56. The ring 55 focuses the electrons from the cathode. As seen in FIG. 4, the fine-wire cathode filament 44 is suspended freely between the base areas 56 of the same metal (e.g. tungsten), over a dished-out region 58 immediately below the filament 44. The conductive metal-filled through holes or vias 48 of FIG. 2 are shown in dashed lines in FIG. 4, for electrically coupling the two ends of the cathode filament to the heater circuit conductors in the dielectric cable.

Figure 4A:
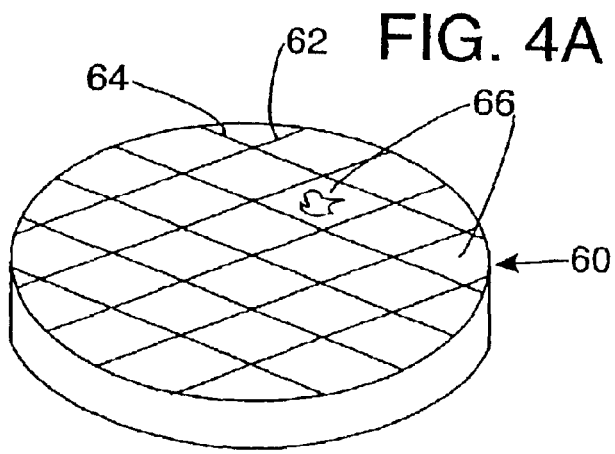

FIGS. 4A through 4E show steps in production of the cathode assembly using MEMS based techniques. FIG. 4A shows a silicon wafer (or other appropriate semiconductor material) 60, and indicates cut lines 62 and 64 for a later division of the wafer into small pieces 66 to produce a number of the desired cathode assemblies. The square pieces 66 will then be cut or ground to circular shape. An alternative approach is to deep etch the assemblies into a round die directly with a backing to release the die, or to place the wafer on a release film before etching.

Figure 4B:
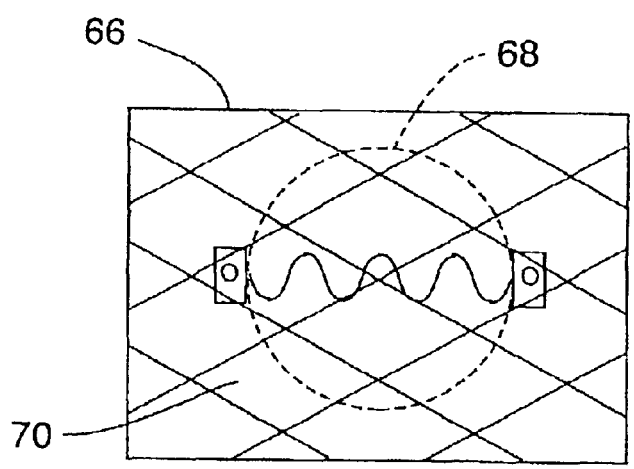

In FIG. 4A, metal is deposited on the surface of the wafer. The entire surface can be deposited with tungsten to produce the filaments, e.g. by chemical vapor deposition or spluttering, and later the majority of the metal can be etched away to form the actual filaments, or a resist can first be applied by using standard semiconductor techniques and then the metal deposited, so as to be located only where desired to form the filament. However, a preferred feature of the invention is to first deposit gold on the wafer in a central region where only the actual filament will be formed. FIGS. 4B and 4C show this central region 68 in dashed lines, with the cathode filament 44 indicated above. FIG. 4B shows the wafer piece 66 after cutting, with a first layer of gold deposited only within the central cathode filament region 68, and with an overlayer 70 of tungsten on the entire wafer piece. Thus, after these small regions 68 are coated with gold onto the wafer, the entire wafer 60 of FIG. 4A can be deposited with tungsten; or, the resist method noted above can be used. At this point, the cathode 44 has not yet been formed, although its position is indicated in FIG. 4B.

FIG. 4C shows the cathode 44 after the excess tungsten, as well as the excess gold, has been etched away. The filament 44 has the integral conductive pads 56 connected to both ends, for connection as explained above to the flexible probe line. The region 68 (dashed lines) within which the gold was deposited as a first layer is also indicated in FIG. 4C, because the tungsten filament 44 has a back layer of gold in this region; this will be the location of a dished out recess 58 after further steps in the MEMS-based production process.

FIG. 4D shows the wafer piece or cathode assembly 66 in cross section, after shaping into a round disk and shows the area in the wafer below the cathode 44 dished out into a recess 58 as also shown in FIG. 4. This can be done by etching, with an etching agent which will leave the cathode filament intact. This agent has to remove material directly under the cathode, so as to leave the cathode freely suspended over the recess 58. FIG. 4D indicates a layer 72 of gold on the bottom side of the cathode filament 44, the purpose of this gold layer being to deposit this gold as a reflective coating 74 on the surface of the recess 58, for better efficiency of the cathode assembly. Once the recess 58 is formed by etching, the cathode assembly 20 is placed in a vacuum system and the filament is heated. The gold evaporates off the back of the filament 44 and coats the bottom of the cavity. The heat is sufficiently high to evaporate the gold thus transferring it onto the surface of the cavity as the reflective layer 74. This transfer process can be carried out after the tube is assembled if the low work function coating is applied only to the front surface of the filament.

The schematic section view of FIG. 4E shows the cathode assembly 20 with the extractor cup 54 and with the cathode assembly secured to the end of the probe line 16. It is important that the high-potential ring 55 formed on the downstream end of the extractor cup be spaced a prescribed distance out from the cathode filament 44, since this ring acts as a weak lens in repelling electrons issued from the cathode so as to tend to converge the flow of electrons en route to the anode. The optimum spacing of this circular ring electrode from the cathode can be determined by calculation or experimentation. In any event, this tends to require relatively thick extractor cup 54, preferably formed by growing layers, 54a, 54b, etc., onto the annulus of the cathode assembly 20, surrounding the cathode 44. One known technique for building thick layers of silicon dioxide has been to alternate the $SiO_2$ layers with another material. For example, the thickness of the extractor cup 54 might be about 0.150 mm, on a cathode assembly of about 0.35 mm diameter, and for a cathode to anode spacing of about 5 mm.

The ring electrode 55, as noted above, is connected to only one side of the cathode, at the conductive base or pad 56, so that this ring is at the cathode potential (plus or minus the small cathode heater voltage), so that the ring does not short the cathode heater circuit.

The growing of the extractor cup layer by layer should be performed before the formation of the recess 58 below the cathode filament due to semiconductor processing constraints. The step of forming this extractor cup, if done by growing layers, should be undertaken just after the cathode and contact pads 56 have been formed by metal deposition and etching. Once the cup has been built, the conductive via or trench 57 is formed to establish a conductive path, then the ring electrode 55 is deposited on the downstream face of the cup. Finally, the silicon dioxide below the cathode filament 44 is etched away to form the dished out recess 58 and thus to position the cathode in free space. For this etching, a resist is used to protect the filament. The process can employ an etching agent to which the tungsten and gold filament is immune.

As shown in FIG. 4E, a small channel 78 can be formed from the recess 58 to the back end of the cathode assembly, through the semiconductor material, for the purpose of pyrometry feedback from the cathode, through the optical fiber probe line 16 to the controller. This feedback gives information as to the temperature at which the cathode is operating enabling control of the x-ray tube output. Alternatively, an entire cylindrical region below the cathode 44 could be removed, replacing the recess 58 and permitting pyrometry. This alternative is less efficient, since little of the cathode's energy would then be reflected in the direction of the anode.

FIG. 4E also shows the cathode assembly 20 secured to the end of the optical fiber probe line 16. The electrical contacts associated with this connection are discussed above, connecting the heater circuit to the central conductors of the optical fiber. The bonding of the two components together can be by conductive glass, solder glass, solid state diffusion, external laser-brazing, by sending a laser beam through the optical fiber 16 to melt and fuse the material, or other methods for securing glass to ceramic.

FIG. 5 shows a variation of a cathode filament 44a, wherein the filament ribbon is formed in a vertical configuration as shown, i.e., the ribbon's width extends parallel to the direction of electron travel. This can be made with a somewhat more complicated etching procedure. With the filament ribbon 44a angled in this direction, the filament has more strength against deflection inwardly toward the dish-out region 58 seen, for example, in FIGS. 4C, 4D and 4E. However, the ribbon will be more compliant in the direction side to side as seen in FIG. 5.

FIG. 6 shows an alternative to the connection arrangement shown in FIG. 4E, with an interposer 80 between the distal end of the glass fiber probe line 16 and the proximal end of the cathode assembly 20. This interposer 80 is for the purpose of making the appropriate electrical connections for the heater circuit wires, enabling transition to a different conductor spacing and facilitating assembly.

FIG. 2 shows the cable 16, with the cathode assembly 20 at its tip, secured to the cylindrical casing 40 of the x-ray tube 18. The connection between the optical fiber 36 and the x-ray tube 40 can be made using solder glass or a series of graded solder glasses, generally shown at 82. One technique is to spin the optical fiber 36 and the tube as the solder glass 82 is melted, for even distribution. The annular bead of solder glass can be made larger than the internal diameter of the tube shell 40, then the material 82 can be melted at its extremities sufficiently that the x-ray tube can be forced over and thus fused together with it.

FIG. 7 shows the fiber optic probe line cable 16 encased within a polymer tube 90. The entire probe has several channels 92, 94, 96 and 98, for various purposes. For example, the channel 92 might carry saline solution for cooling; the smaller channel 94 might carry solution or fluid for blowing up one or more balloons for centering purposes, and another channel 96 can be for return of saline coolant. Additionally channels 98 and 100 are indicated. A thermocouple could be threaded through one or more of the channels.

The above described preferred embodiments are intended to illustrate the principles of the invention, but not to limit its scope. Other embodiments and variations to this preferred embodiment will be apparent to those skilled in the art and may be made without departing from the spirit and scope of the invention as defined in the following claims.

I claim:

1. A miniature x-ray tube device for use in delivering an x-ray dosage from the end of an elongated probe line inserted within a space in living tissue, comprising:
    a vacuum enclosure at a distal end of the probe line, defining a vacuum chamber, and the vacuum chamber including a thermionic cathode connected via heater conductors in a cathode heating circuit, and including a target and an anode spaced from the cathode and connected to a high-voltage conductor and positioned to receive electrons from the cathode when the cathode is heated by current delivered through the heater conductors in said heating circuit and when a high voltage potential is applied via the high-voltage conductor and one of the heater conductors, and
    the cathode being a fine-wire cathode produced by MEMS technology and comprising a filament of thin, flat configuration suspended on an etchable semiconductor substrate, an area of the substrate between ends of the filament having been etched away such that the filament hangs in free space supported by filament ends which are secured to the substrate.

2. The device of claim 1, wherein the cathode has a resistance of at least about 100 ohms.

3. The device of claim 1, wherein the probe line comprises a glass fiber carrying the conductors, the fiber being of dielectric material.

4. The device of claim 1, wherein the heater conductors carrying current in the heating circuit for the cathode are fine wires of about 1–4 mil (0.025–0.102 mm) diameter.

5. The device of claim 4, wherein the fine wires are of tungsten, molybdenum, copper, gold, gold-coated tungsten, or gold-coated molybdenum.

6. The device of claim 1, wherein the high-voltage conductor comprises an outer ground sheath on the probe, connected to the anode, and where in the heater conductors are contained within the probe, interior to the outer sheath.

7. The device of claim 6, wherein the high-voltage conductor carries high voltage of at least about 20 kV, which is also carried on one of said heater conductors, connected to a high voltage power supply.

8. The device of claim 1, wherein the high-voltage conductor carries high voltage of at least about 10–15 kV, which is also carried on one of said heater conductors, connected to a high voltage power supply.

9. The device of claim 1, wherein the heater conductors are positioned generally centrally within the probe, the high-voltage conductor comprising a coaxial outer conductor surrounding the heater conductors and insulated therefrom by dielectric material.

10. A miniature x-ray tube device for use in delivering an x-ray dosage from the end of an elongated probe inserted within a space in living tissue, comprising:
    a vacuum enclosure at a distal end of the probe line, defining a vacuum chamber, and the vacuum chamber including a thermionic cathode connected via heater conductors in a cathode heating circuit, and including a target and an anode spaced from the cathode and connected to a high-voltage conductor and positioned to receive electrons from the cathode when the cathode is heated by current delivered through the heater conductors in said heating circuit and when a high voltage potential is applied via the high-voltage conductor and one of the heater conductors,
    the cathode being a fine-wire cathode produced by MEMS technology, and
    wherein the MEMS-produced cathode includes an extractor cup positioned to direct electrons from the cathode toward the anode, the cathode and extractor cup being integrally formed in a wafer.

11. A method for producing a miniature x-ray tube on an elongated probe for use in delivering an x-ray dosage within a space in living tissue, comprising:
    depositing a layer of metal cathode filament material on a semiconductor substrate,
    etching away all but the desired filament from the deposited metal layer,
    etching away an area of the substrate supporting the filament such that the cathode filament hangs in free space supported by two filament ends which are secured to the substrate,
    providing an elongated flexible probe carrying three conductors, including first, second and third conductors,
    securing to a distal end of the probe the cathode and supporting substrate, and providing a vacuum enclosure so as to surround the cathode within a vacuum chamber defined by the vacuum enclosure, and the vacuum enclosure including an anode and target spaced from the cathode,
    connecting the first and second conductors of the probe to the cathode in a cathode heating circuit, and
    connecting the anode to the third conductor so that a high voltage potential can be placed between the cathode and the anode via the third conductor and one of said first and second conductors.

12. The method of claim 11, wherein the cathode filament comprises a tungsten filament formed in an undulating shape.

13. The method of claim 11, further including providing an electron extractor cup surrounding the cathode and extending outwardly from the substrate, toward the anode.

14. The method of claim 13, wherein the extractor cup has an annulus of metal conductor, electrically connected to the cathode, and positioned on the extractor cup so as to help focus a stream of electrons from the cathode en route to the anode.

15. The method of claim 11, further including operating the miniature x-ray tube by passing current through the cathode heating circuit to heat the cathode, thereby driving off electrons, and including placing high voltage potential between the cathode and the anode in the high voltage circuit, such that the driven-off electrons are accelerated to the anode and target, producing x-rays.

16. The method of claim 11, wherein the flexible probe comprises an optical fiber carrying the conductors, the fiber being of dielectric material.

17. The method of claim 16, wherein the conductors within the optical fiber are generally D-shaped in cross section, with flat sides of the D-shapes arranged back to back and spaced apart.

18. The method of claim 16, further including fusing the cathode supporting substrate to the end of the optical fiber.

19. The method of claim 11, further including providing an electron extractor cup surrounding the cathode and extending outwardly from the substrate toward the anode, and including forming the extractor cup by building successive layers on the cathode supporting substrate.

20. The method of claim 11, wherein the first and second conductors carrying current in the heating circuit for the cathode are fine wires of about 37 gauge.

21. The method of claim 11, wherein the flexible probe comprises glass fiber of dielectric material, and wherein the third conductor comprises a ground conductor coaxially surrounding the optical fiber, the distance between the first or second conductor to the ground being less than about 400–500 microns.

22. The method of claim 11, further including the step of depositing a layer of gold on the semiconductor substrate prior to the step of depositing a layer of metal cathode filament material, and further including the step, subsequent to etching away an area of the substrate, of heating the cathode to drive off the gold from the filament to thereby coat at least a portion of the substrate adjacent to the freely hanging filament, thereby forming a reflector surface behind the cathode filament.

23. The method of claim 11, further including the step of providing a focusing ring spaced outwardly from the cathode and at high potential, the focusing ring being on the surface of an extractor cup.

24. The method of claim 23, when the extractor cup is formed to include a through via extending down to a high voltage conductor adjacent to the cathode filament, and including filling the through via with conductive metal as the focusing ring is deposited.

25. A method for producing a cathode for a miniature x-ray tube, comprising:
 depositing a layer of metal cathode filament material on a semiconductor substrate,
 etching away all but the desired filament from the deposited metal layer,
 etching away an area of the substrate supporting the filament such that the cathode filament hangs in free space supported by two filament ends which are secured to the substrate, and
 providing conductors on the semiconductor substrate in position for connection to a heater circuit on a probe to which the x-ray tube is to be connected.

26. The method of claim 25, wherein the cathode filament comprises a tungsten filament formed in an undulating shape.

27. The method of claim 25, further including providing an electron extractor cup surrounding the cathode and extending outwardly from the substrate.

28. The method of claim 27, wherein the extractor cup has an annulus of metal conductor, electrically connected to the cathode, and positioned on the extractor cup so as to help focus a stream of electrons from the cathode en route to an anode.

29. The method of claim 25, further including providing an electron extractor cup surrounding the cathode and extending outwardly from the substrate toward the anode, and including forming the extractor cup by building successive layers on the cathode supporting substrate.

30. The method of claim 25, further including the step of depositing a layer of gold on the semiconductor substrate prior to the step of depositing a layer of metal cathode filament material, and further including the step, subsequent to etching away an area of the substrate, of heating the cathode to drive off the gold from the filament to thereby coat at least a portion of the substrate adjacent to the freely hanging filament, thereby forming a reflector surface behind the cathode filament.

31. The method of claim 25, further including the step of providing a focusing ring spaced outwardly from the cathode and at high potential, the focusing ring being on the surface of an extractor cup.

32. A cathode for a miniature x-ray tube, produced according to the method of claim 25.

* * * * *